United States Patent
Roest et al.

(10) Patent No.: US 11,547,996 B2
(45) Date of Patent: Jan. 10, 2023

(54) DEVICE AND METHOD FOR LIQUID ANALYSIS TO DETECT BIOMARKERS

(71) Applicant: VITAL SIGNS SOLUTIONS LIMITED, Chatham (GB)

(72) Inventors: Kiran Roest, Geneva (CH); Vladimir Gubala, Chatham (GB)

(73) Assignee: VITAL SIGNS SOLUTIONS LIMITED, Chatham (GB)

( * ) Notice: Subject to any disclaimer, the term of this patent is extended or adjusted under 35 U.S.C. 154(b) by 1011 days.

(21) Appl. No.: 16/323,111

(22) PCT Filed: Aug. 3, 2017

(86) PCT No.: PCT/GB2017/052253
§ 371 (c)(1),
(2) Date: Feb. 4, 2019

(87) PCT Pub. No.: WO2018/025041
PCT Pub. Date: Feb. 8, 2018

(65) Prior Publication Data
US 2019/0168220 A1 Jun. 6, 2019

(30) Foreign Application Priority Data
Aug. 5, 2016 (GB) ..................... 1613504

(51) Int. Cl.
*G01N 21/78* (2006.01)
*B01L 3/00* (2006.01)
*G01N 33/543* (2006.01)

(52) U.S. Cl.
CPC ..... *B01L 3/502715* (2013.01); *B01L 3/50273* (2013.01); *G01N 21/78* (2013.01);
(Continued)

(58) Field of Classification Search
CPC .......... B01L 3/502715; B01L 3/50273; B01L 2200/10; B01L 2300/0654;
(Continued)

(56) References Cited

U.S. PATENT DOCUMENTS 6,180,062 B1 * 1/2001 Naka ................ B01L 3/502723
422/68.1
7,824,879 B2 11/2010 Kahn et al.
(Continued)

FOREIGN PATENT DOCUMENTS

EP 0803288 A2 10/1997
EP 2733356 A1 5/2014
(Continued)

OTHER PUBLICATIONS

International Search Report and Written Opinion of the International Searching Authority for PCT/GB2017/052253 dated Oct. 25, 2017.
(Continued)

*Primary Examiner* — Matthew D Krcha
*Assistant Examiner* — Sophia Y Lyle
(74) *Attorney, Agent, or Firm* — Heslin Rothenberg Farley & Mesiti P.C.

(57) ABSTRACT

A device enables a user to detect biomarkers, and includes an element that defines a multiplicity of microfluidic channels that communicate between an inlet duct and an outlet duct, the inlet duct communicating with an inlet port into which a user can introduce a drop of body fluid; the outlet duct communicating with an outlet port. A resilient bladder is connected to the outlet port to provide suction. Each microfluidic channel defines a reaction chamber containing a biomarker-sensitive reagent which provides a color or a change of color in the presence of a biomarker, there being a multiplicity of different biomarker-sensitive reagents, one
(Continued)

such biomarker-sensitive reagent being provided in each of the multiplicity of different microfluidic channels. At least part of the element is transparent so the color within the reaction chamber can be seen. The device includes a cover with magnifying lenses above the reaction chambers. The device may be used in conjunction with a smart phone.

18 Claims, 2 Drawing Sheets

(52) U.S. Cl.
CPC .... *G01N 33/54366* (2013.01); *B01L 2200/10* (2013.01); *B01L 2300/0654* (2013.01); *B01L 2300/0681* (2013.01); *B01L 2300/0816* (2013.01); *B01L 2300/0864* (2013.01); *B01L 2300/0887* (2013.01); *B01L 2400/049* (2013.01); *B01L 2400/0481* (2013.01); *B01L 2400/0688* (2013.01)

(58) Field of Classification Search
CPC ..... B01L 2300/0681; B01L 2300/0816; B01L 2300/0864; B01L 2300/0887; B01L 2400/0481; B01L 2400/049; B01L 2400/0688; G01N 21/78; G01N 33/54366
See application file for complete search history.

(56) References Cited

U.S. PATENT DOCUMENTS

| | | | | |
|---|---|---|---|---|
| 2001/0029794 | A1* | 10/2001 | Frye | B01L 3/50853 73/864.81 |
| 2002/0064480 | A1* | 5/2002 | Shartle | B01L 3/5027 422/400 |
| 2005/0106066 | A1* | 5/2005 | Saltsman | G01N 33/5304 422/504 |
| 2007/0099290 | A1* | 5/2007 | Iida | B01L 3/502746 977/900 |
| 2007/0209935 | A1* | 9/2007 | Vogel | G01N 33/48728 204/403.01 |
| 2010/0105577 | A1 | 4/2010 | Dugan et al. | |
| 2010/0213062 | A1 | 4/2010 | Guzman | |
| 2013/0084630 | A1* | 4/2013 | Rolland | G01N 33/543 435/287.8 |
| 2013/0189166 | A1* | 7/2013 | Thomas | G01N 31/22 156/60 |
| 2013/0260372 | A1 | 10/2013 | Buermann et al. | |
| 2014/0176939 | A1 | 6/2014 | Shah et al. | |
| 2015/0185159 | A1 | 7/2015 | Hirao et al. | |
| 2015/0260719 | A1* | 9/2015 | Godec | B01L 3/5085 436/63 |

FOREIGN PATENT DOCUMENTS

| | | |
|---|---|---|
| WO | 2008002483 A2 | 1/2008 |
| WO | 2011157981 A1 | 12/2011 |
| WO | 2015038717 A1 | 3/2015 |

OTHER PUBLICATIONS

United Kingdom Search Report for Great Britain Application No. GB1613504.8 dated Feb. 3, 2017.

* cited by examiner

DEVICE AND METHOD FOR LIQUID ANALYSIS TO DETECT BIOMARKERS

CROSS REFERENCE TO RELATED APPLICATIONS

This application is a national stage filing under section 371 of International Application No. PCT/GB2017/052253, filed on Aug. 3, 2017, published in English on Feb. 8, 2018 as WO2018/025041A1, and claims priority to Great Britain Application No. 1613504.8, filed on Aug. 5, 2016. The entire disclosures of each application are hereby incorporated herein by reference.

The present invention relates to a device and a method for liquid analysis, using microfluidic technology to detect biomarkers, for example in blood plasma.

BACKGROUND

In modern society there is an increasing incidence of preventable diseases, also referred to as lifestyle diseases, which can be caused or significantly worsened by obesity, poor diet or lack of exercise. Increasing prosperity tends to lead to an increase in unhealthy behaviour and lifestyle diseases. At the same time there is an overall trend towards an ageing population, and this makes it critical to address such preventable diseases or health systems worldwide will become increasingly strained. Lifestyle diseases include type II diabetes, cardiovascular disease, stroke, kidney disease and gout, and the likelihood of any person suffering from any one of these is dramatically reduced through lifestyle modification: a healthy diet, maintaining a healthy body mass index, and regular exercise.

It is therefore becoming imperative to find cost-effective ways of improving patient health. For example the UK's NHS has started to offer a basic health check which includes testing a large number of blood and urine-derived biomarkers associated with lifestyle diseases, once every 5 years to people over the age of 40. They estimate that this can deliver very significant annual savings as a direct result of improved patient health. Similar approaches are being adopted in the USA.

It is also the case that consumer adoption of digital technology has seen significant innovation in personal health management. The major technical developments here relate to wearable and Wi-Fi-linked technology combined with smart phones. For example wearable devices enable users to track energy usage, and activity level for various different types of exercise, and in some cases also heart rate; Wi-Fi-linked technology enable a user's weight or blood pressure to be monitored. Such developments mean that patients can become important stakeholders in the management of their own health.

It would therefore be advantageous if consumers could be provided with a device to enable them to check and track biomarkers that indicate risk of major preventable diseases, in particular those biomarkers that can be modified through changes in lifestyle. Similar technology might also be used by consumers in other contexts, for example specific biomarkers may be monitored to enable female fertility or pregnancy to be tracked.

BRIEF SUMMARY OF THE INVENTION

According to the present invention there is provided a device for enabling a user to detect biomarkers, the device comprising an element that defines a multiplicity of microfluidic channels that communicate between an inlet duct and an outlet duct; the inlet duct communicating with an inlet port at a surface of the element into which a user can introduce a drop of body fluid; the outlet duct communicating with an outlet port at a surface of the element, the device also incorporating means connected to the outlet port to provide suction; wherein each microfluidic channel defines a reaction chamber containing a biomarker-sensitive reagent which provides a colour or a change of colour in the presence of a biomarker, there being a multiplicity of different biomarker-sensitive reagents, one such biomarker-sensitive reagent being provided in each of the multiplicity of different microfluidic channels, and at least part of the element being transparent so that the colour or change of colour within the reaction chamber can be viewed from outside the element.

The term microfluidic channel refers to a channel with a transverse dimension significantly less than 1 mm, more preferably less than 250 µm, for example 100 µm or 50 µm. By using such a narrow channel, only a small amount of body fluid needs to be introduced into the inlet port.

The term body fluid refers to a liquid that can easily be obtained from a person, such as urine, saliva, sweat or blood, and which may be expected to contain biomarkers of relevance to the person's health. If the body fluid to be tested is blood, then the inlet duct will also incorporate a filter to separate plasma from the blood.

Thus as the body fluid is sucked out of the inlet port, it flows along the inlet duct and then flows in parallel into and along each of the multiplicity of microfluidic channels that communicate between the inlet duct and the outlet duct. The only liquid in the device is from the body fluid introduced into the inlet port. The means to provide suction may be a resilient elastomeric bladder. Before use this would be in a compressed state, and after introducing the drop of body fluid into the inlet port the elastomeric bladder would be allowed to expand, so sucking body fluid into the inlet duct and so through the multiplicity of microfluidic channels. Fluid flow in the device takes place only as a consequence of expansion of the elastomeric bladder, and when the bladder has reached its expanded state the flow will cease.

Each microfluidic channel may also enclose a porous hydrophobic element downstream of the reaction chamber, such when any aqueous liquid has flowed through the reaction chamber to reach the porous hydrophobic element, further flow along the microfluidic channel is inhibited. This helps to ensure that fluid flows through each of the multiplicity of microfluidic channels.

For ensuring the colours are clearly visible, the element may be of laminated construction, comprising a white substrate below the microfluidic channels, with a transparent material covering the microfluidic channels.

The device may also incorporate a cover, the cover defining multiple lenses that are above the reaction chambers. These lenses may be arranged to make the reaction chambers appear larger, so the colour or change of colour is easier to see. The cover may also include an openable flap that covers the suction means; and also an aperture aligned with the inlet port.

The colour or change of colour may be observed by eye, and the colour may be compared to a colour chart to enable the presence or concentration of the biomarker to be deduced. Alternatively the device of the invention may be used in conjunction with a smart phone that includes a camera, the camera being used to view the colours of the reaction chambers, as viewed through the cover where this is provided. The camera may be used only to record the information about the colours, or the smart phone may include a software application that is used to deduce from the observed colours information about each of the biomarkers, and to convey that information to the end user. When using a camera it may also be advantageous to provide a colour chart or a strip of different colours, for example on the cover, to be viewed at the same time as the colour in the reaction chamber is being monitored, as this may help the accurate monitoring of the colours, to take into account for example ambient lighting and the sensitivity of the camera. In some cases the colour of the biomarker-sensitive reagent may indicate merely the presence or absence of the biomarker, while in other cases the colour of the biomarker-sensitive reagent may indicate the concentration of the biomarker.

Thus in one specific example the user may use a small lancet or needle to prick their finger and to obtain a drop of blood, and the user would introduce the drop of blood into the inlet port, which may for example have a capacity less than 100 μL, for example in the range 20 to 50 μL. The user would then activate the suction means, for example by opening the flap so that the resilient bladder expands and sucks the blood along the inlet duct, so plasma flows through the filter and then into the reaction chambers of each of the microfluidic channels. After allowing sufficient time for the plasma to reach each reaction chamber, and for each of the reactions to occur, the user would then view the colours or the changes of colours of each reaction chamber, for example using a smart phone.

The aim of the device is to enable the user to monitor the levels of biomarkers that are of relevance to them. In one example the biomarkers are related to overall health, and can be affected by modifications to the user's lifestyle. Considering blood as the body fluid of interest, there are a number of different biomarkers which correlate with specific diseases or health issues, for example cardiovascular disease (e.g. lipids), type II diabetes (e.g. glucose, HbA1c), chronic kidney disease (creatinine), anaemia (haemoglobin), gout (uric acid), liver health (gamma GT), and general nutritional health (vitamin D, B12 and folic acid). As another example the biomarkers may be selected as indicative of fertility, and in this case the device would enable the user to monitor normal hormonal fluctuations. In another example the biomarkers may be selected as indicative of sports health or sports performance; or the device may be used for the detection of performance-enhancing substances.

In a second aspect, the invention relates to a method for liquid analysis, using the device as indicated above to detect biomarkers, for example in blood plasma.

In a third aspect, the invention provides a method for liquid analysis, using microfluidic technology to detect multiple biomarkers by colorimetric reactions, wherein the biomarkers are selected from: lipids, glucose, HbA1c (i.e. glycated haemoglobin), creatinine, haemoglobin, uric acid, gamma GT (i.e. gamma glutamyl transferase), vitamin D, vitamin B12, and folic acid. Preferably at least six such biomarkers are selected and detected, so a plurality of lifestyle diseases can be monitored. It will be appreciated that, in addition, other biomarkers may also be detected.

The invention will now be further and more particularly described, by way of example only, and with reference to the accompanying drawings, in which.

Figure 1:
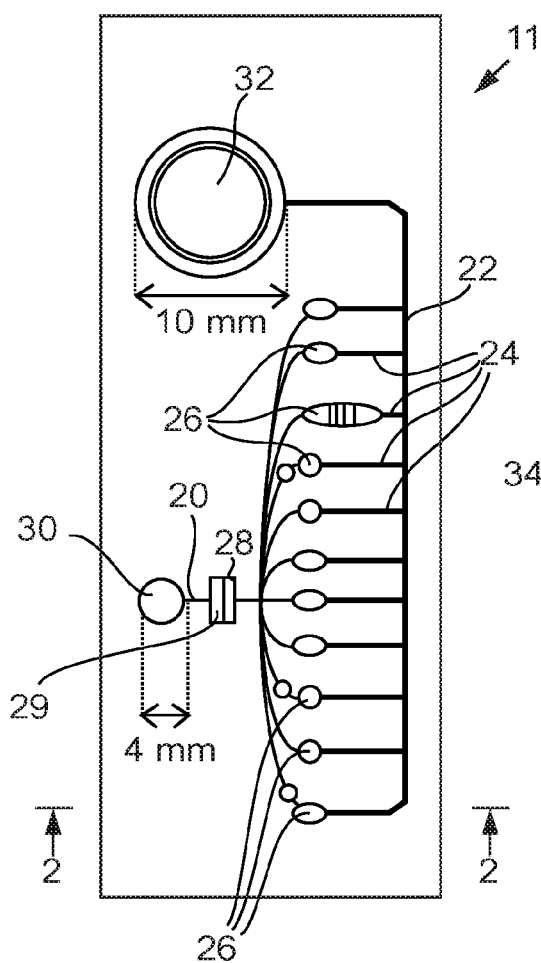
FIG. 1 shows a plan view of an element of a detection device of the invention.
Figure 2:
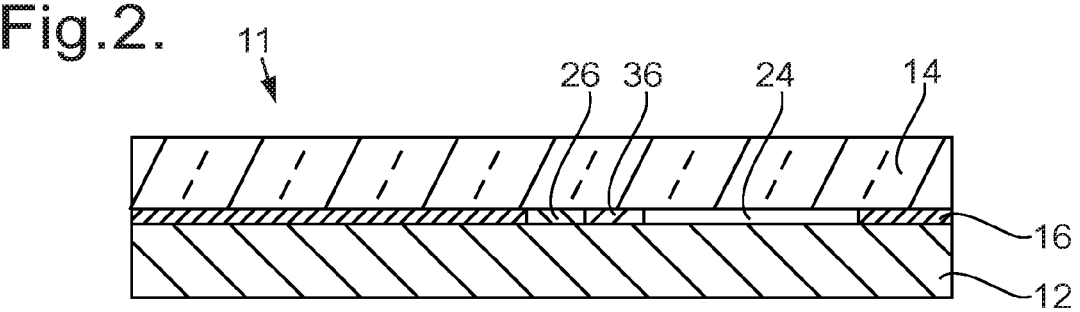
FIG. 2 shows a cross-sectional view on the line 2-2 of FIG. 1 (not to scale)

Referring now to FIG. 1, a detection device 10 (shown for example in FIG. 3b) comprises a rectangular element 11 of laminated structure formed of poly-methylmethacrylate (PMMA); in this example the rectangular element 11 is 25 mm wide and 70 mm long, which is the same as the dimensions of a standard microscope slide. Referring also to FIG. 2, the device 10 consists of a base sheet 12 of white PMMA, and a top sheet 14 of transparent PMMA, which are held together by a layer 16 of pressure sensitive adhesive (PSA) of thickness 50 μm. Before assembly, the layer 16 is cut out so as to define an inlet channel 20, an outlet channel 22, and eleven microfluidic channels 24 for parallel fluid flows between the inlet channel 20 and the outlet channel 22. Each microfluidic channel 24 also includes a somewhat wider reaction chamber 26; in this example all the reaction chambers 26 are in a straight line.

By way of example the inlet channel 20, the outlet channel 22 and each microfluidic channel 24 may be of width 1 mm (as seen in plan view), while the reaction chambers 26 may be of width 2 mm. The inlet channel 20 also defines a filtration chamber 28 of width 4 mm but of length only 2 mm. A pad 29 of microporous nitrocellulose membrane of thickness 50 μm and 2 mm×4 mm in plan is placed in this filtration chamber 28. Appropriately sized microporous pads may be placed within at least some of the reaction chambers 26.

The top sheet 14 defines an inlet port 30, which may be of diameter 4 mm at the surface, tapering to 1 mm where it communicates with the inlet channel 20; at the bottom of the inlet port 30 is a very thin layer of paper (significantly less than 50 μm thick). The top sheet 14 also defines an outlet port 32 which may be of diameter 10 mm. The inlet port 30 and the outlet port 32 may be cut out of the top sheet 14 for example using a $CO_2$ laser. The outlet channel 22 leads to a circular space aligned with the outlet port 32 and of the same diameter as the outlet port 32.

Figure 1A:
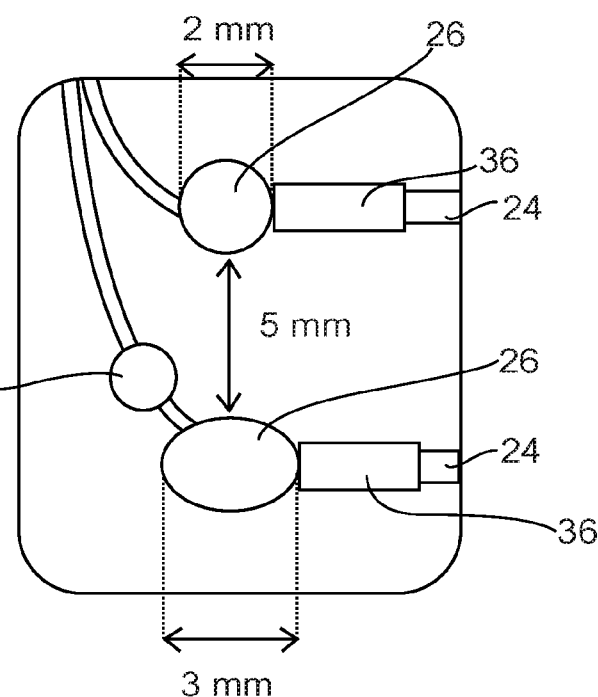
FIG. 1a shows a plan view of part of the element of FIG. 1 to a larger scale.

Referring now to FIG. 1a (in which the two reaction chambers 26 nearest the bottom of FIG. 1 are shown to a larger scale), the microfluidic channels 24 define reaction chambers 26, each of which contains a specific biomarker-sensitive reagent, and there are 5 mm gaps between adjacent reaction chambers 26. In some cases there is a pre-reaction chamber 34 upstream of the reaction chamber 26, which may also contain a suitable reagent. And in each case downstream of the reaction chamber 26 is a hydrophobic valve 36 in the form of a 1.2 mm wide section of channel within which is placed a wax-impregnated piece of chromatography paper 1.2 mm wide, 2 mm long and of thickness 50 μm. In this example each hydrophobic valve 36 is at the outlet from each reaction chamber 26, so aqueous body fluids can flow into the reaction chamber 26 but do not flow beyond the reaction chamber 26 along the microfluidic channel 24. Before attaching the top sheet 14 the pad 29 is inserted into the filtration chamber 28; any microporous pads that are required are inserted into the reaction chambers 26; the wax-impregnated strips are placed into the hydrophobic valves 36; and the requisite biomarker-sensitive reagents are introduced into the reaction chambers 26 and where necessary into the pre-reaction chambers 34. The top sheet 14 is then attached, being securely held by the adhesive properties of the layer 16.

Figure 3A:
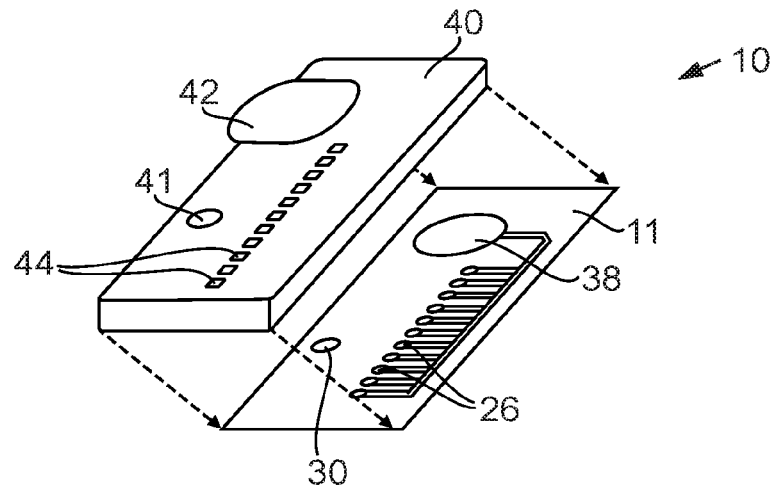
FIG. 3a shows an exploded perspective view of the detection device, which includes the element of FIG. 1, along with a cover.

Referring now to FIG. 3a, the device 10 consists of the element 11 described above, along with a resilient elastomeric bladder 38; in this example the device 10 also includes a cover 40. The bladder 38 is mounted in and bonded to the outlet port 32, and after being fixed in position in this way, the bladder 38 is squeezed down into a compressed state (as shown). The cover 40 encloses the element 11 on its top and sides, so protecting the element 11, and may be of an opaque plastic material. The cover 40 defines an aperture 41 which is aligned with the inlet port 30, and it includes a hinged flap 42 which covers the resilient elastomeric bladder 38. In addition the cover 40 defines a row of a square lenses 44 of PMMA, each of which is convex on its lower surface and flat on its upper surface so as to act as a magnifying lens, and is directly above one of the reaction chambers 26. The cover 40 is shown in FIG. 3a separated from the element 11, but in reality the element 11 is enclosed by the cover 40, so the elastomeric bladder 38 is held in its compressed state by the hinged flap 42 of the cover 40.

Figure 3B:
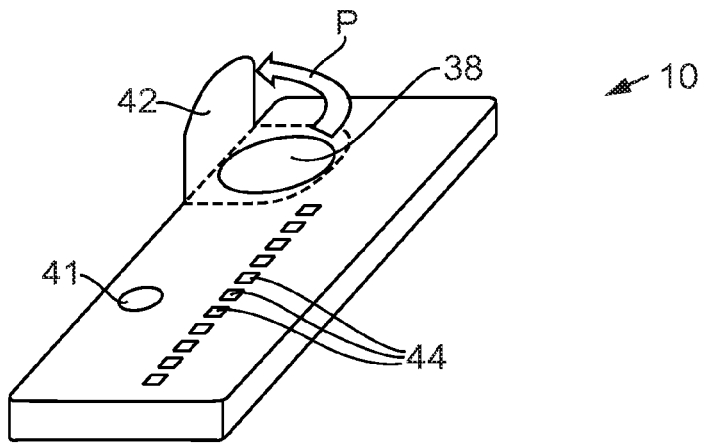
FIG. 3b shows a perspective view of the detection device with its cover, during operation.
Figure 3C:
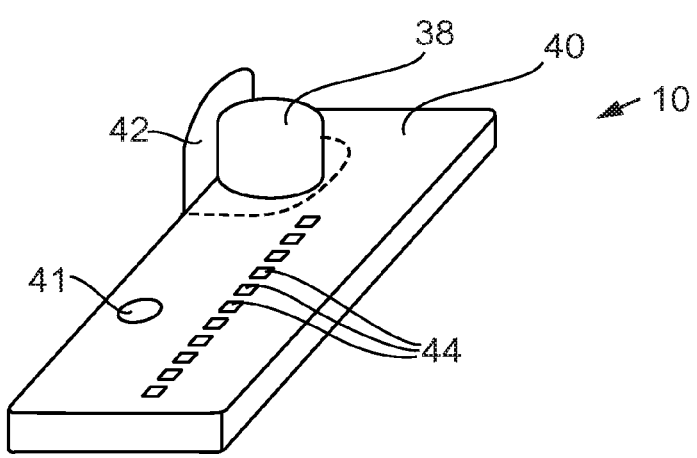
FIG. 3c shows a perspective view of the detection device with its cover, when operation has completed.

In use the user would first prick their finger with a needle or small lancet to produce a drop of blood, and deposit the drop of blood through the aperture 41 into the inlet port 30. Then, as shown in FIG. 3b, the user would lift the hinged flap 42 as indicated by the arrow P so the elastomeric bladder 38 is no longer covered and held down. Consequently, as shown in FIG. 3c, the elastomeric bladder 38 expands, and in so doing sucks the drop of blood through the inlet channel 20, and consequently sucks the blood plasma through the microfluidic channels 24 into each of the reaction chambers 26. A small amount of the blood is absorbed into the thin sheet of paper at the bottom of the inlet port 30.

There are consequentially colours formed, or changes of colour, in the reaction chambers 26 indicating the detection of the corresponding biomarkers, and the resulting colours can be viewed through the row of lenses 44. By way of example the user may use a smart phone camera to view the row of lenses 44, the smartphone including a software application for analysing the colours to deduce information about the biomarkers.

The device 10 is shown by way of example only, and may be modified in several ways while remaining within the scope of the invention. In particular the device 10 may differ structurally from that described above, for example the layer 16 which bonds together the base sheet 12 and the top sheet 14, and which determines the thickness of the channels 20, 22 and 24, may for example be of thickness 100 μm rather than 50 μm. The arrangement of the various channels 20, 22 and 24 may differ from that shown, as may the dimensions of the element 11. For example there may be a different number of microfluidic channels 24, and they may be arranged so that the reaction chambers 26 are in a different arrangement for example lying along a circular arc. The dimensions of all the flow channels may differ from those described above, and the device may be constructed in a different way to that described above. For example if a device is required to monitor only five biomarkers it would only require five microfluidic channels 24 with five reaction chambers 26, and consequently only five lenses 44.

Figure 1B:
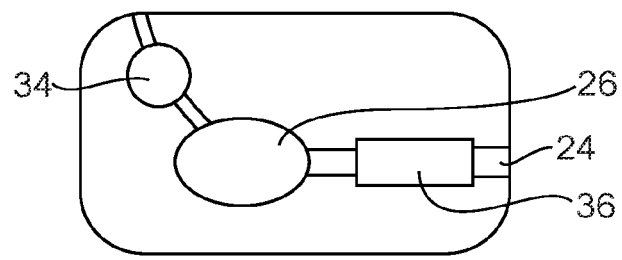
FIG. 1b shows a plan view of part of a modification to the element of FIG. 1 to a larger scale.

In the device 10 each hydrophobic valve 36 is at the outlet from each reaction chamber 26, so aqueous body fluids can flow into the reaction chamber 26 but do not flow beyond the reaction chamber 26 along the microfluidic channel 24. In a modification there may be a section of microfluidic channel 24 between each reaction chamber 26 and the associated hydrophobic valve 36, and such a modification is shown in FIG. 1b to which reference is now made. The distance along the microfluidic channel 24 between the reaction chamber 26 and the hydrophobic valve 36 may be between 0 mm and 6 mm, for example 3 mm or 5 mm, and it has been found that this distance provides a somewhat more uniform colour in the reaction chamber 26 than is obtained where the hydrophobic valve 36 is immediately next to the reaction chamber 26. On the other hand, the greater the distance along the microfluidic channel 24 between the reaction chamber 26 and the hydrophobic valve 36, the more liquid needs to be introduced into the device 10.

Colorimetry

Each reaction chamber 26 is provided with a reagent that is sensitive to a particular biomarker, and which produces a well-defined colour or colour change in the presence of that biomarker. The white colour of the base sheet 12 helps ensure a clear contrast where the colour is formed. The reagents and the corresponding colours will depend upon which biomarkers are to be detected and monitored, and the reagents are deposited and dried on the base sheet within the reaction chamber 26 or on a porous pad within the reaction chamber 26 during production of the element 11, or in some cases in a pre-reaction chamber 34. Some suitable reagents and colour changes are described as follows by way of example only, all the reagents referred to being commercially available.

1. Cholesterol, LDL, HDL, TG (triglycerides)—Lipoproteins transport the majority of plasma lipids including cholesterol and triglycerides within the bloodstream. The lipoproteins responsible for the vast majority of cholesterol transport in the blood are high-density lipoprotein (HDL), low-density lipoprotein (LDL) and very low density lipoprotein (VLDL). In the device 10 there are three separate reaction chambers 26 which are arranged to detect total cholesterol, non-LDL, and total triglycerides respectively. The clinically relevant concentrations of cholesterol are 140-400 mg/dl.

1a. Total cholesterol can be detected as follows. The majority of the total cholesterol in the blood is in the form of cholesteryl esters. The esters can be hydrolysed to cholesterol by the enzyme cholesterol esterase, printed on a porous pad within the reaction chamber 26. All the cholesterol is then oxidised by the enzyme cholesterol oxidase, also provided on the porous pad within the reaction chamber 26, so producing hydrogen peroxide. The hydrogen peroxide then reacts with a dye precursor such as di-substituted aniline (to form quinone imine dye), so producing colour.

1b. The level of HDL (i.e. not LDL) can be detected as follows. Some of the plasma from the blood sample is directed towards a pre-reaction chamber 34 which contains phosphotungstic acid. This brings about aggregation and precipitation of the lower density lipoproteins, leaving only the HDL in solution. In the following reaction chamber 26 is a porous pad containing cholesterol oxidise along with a dye precursor, so the HDL cholesterol in solution is converted to cholest-4-en-3-one and hydrogen peroxide. The peroxide then reacts with the dye precursor, for example di-substituted aniline to form quinone imine dyes. The colour change from the last reaction can then be imaged by the smartphone camera.

1c. Triglycerides are measured enzymatically by providing the enzyme lipase on a porous pad in a reaction chamber 26, so producing glycerol by hydrolysis. The porous pad also includes the enzyme glycerol oxidase, so the glycerol is oxidised, forming hydrogen peroxide. The quantity of hydrogen peroxide can be detected using a dye precursor as described above.

2. Glucose—in this case the measurement may be based on oxidizing glucose present in blood plasma by glucose oxidase to produce hydrogen peroxide, which then reacts with leuco-precursors of 4-aminoantipyrine and 1,7-dihydroxynaphthalene to produce a red colored dye product. The glucose oxidase enzyme along with the dye precursors may be provided on a porous pad within a reaction chamber 26.

3. HbA1C (i.e. glycated haemoglobin)—in this case the measurement may utilise electrolyte mediated (NaCl) aggregation of anti-HbA1C-Gold nanoparticles (AbGNP) in the absence of HbA1C (the antigen) in plasma. The AbGNP are provided on a porous pad in the reaction chamber 26. The presence of antigen prevents aggregation of functionalized AbGNPs and hence the solution remains red while absence of antigen leads to aggregation resulting in a visible change of colour from red to purple-blue.

4. Uric Acid—Uric Acid may be detected using the enzyme uricase, and peroxidase-like complex of MIL-53 (Fe), these being provided on a porous pad in a reaction chamber 26. The uricase in the presence of water and dissolved oxygen brings about oxidation of the uric acid to 5-hydroxyisourate and hydrogen peroxide. The hydrogen peroxide reacts with the peroxidase-like complex of MIL-53(Fe) to produce a blue colour.

5. Haemoglobin—the level of haemoglobin may be semi-quantitatively detected directly from the colour of the thin piece of paper at the bottom of the inlet port 30. This may use the HbCS (Haemoglobin Colour Scale), by comparing the colour of the blood absorbed in the thin piece of paper with standard colours. Such standard colours may be printed on the cover 40, and may show a range of different colours corresponding to increments in the haemoglobin concentration of 2 g/dl.

6. Creatinine—the semi-quantitative detection of creatinine may be based on Cayman Chemical Creatinine (serum) Colorimetric Assay Kit. The clinically relevant concentration for adult males is in the range of 0.7-1.5 mg/dl. For adult females it is 0.4-1.2 mg/dl. The orange colour developed by a reaction with picric acid can be measured colorimetrically, where the intensity of the obtained colour is directly proportional to the concentration of creatinine in the sample.

7. Gamma GT (i.e. gamma glutamyl transferase, or GGT)—gammaGT activity may be determined by a coupled enzyme assay, in which the GGT transfers the γ-glutamyl group from the substrate L-γ-Glutamyl- p-nitroanilide, liberating the chromogen p-nitroanilide (pNA) proportional to the GGT present. One unit of GGT is the amount of enzyme that will generate 1.0 µmol of pNA per minute at 37° C.

8. Folic acid—The clinically relevant range is 2.7-17.0 ng/ml. The measurement may be based on the use of the gold nanoclusters (AuNCs) and cysteamine-modified gold nanoparticles (cyst-AuNPs). This is due to aggregation of the cyst-AuNPs induced by folic acid, which shifts the absorption peaks from 530 to 670 nm. The colour intensity of the AuNCs/cyst-AuNPs system is proportional to the concentration of folic acid in the range from 1.1 to 227 nmol/L.

9. Vitamin D—the semi-quantitative detection of vitamin D may be based on tracking of 25(OH)D (i.e. 25-hydroxyvitamin D) in serum. The detection may be based on gold nanoparticle (AuNP) based colorimetric competitive direct-antigen immunoassay, for example as described by Lee et al. in *Lab Chip*, 2014, 14, 1437. This assay enables 25(OH)D molecules to be quantified, as their small size (~400 g/mol) means they can bind to not more than one antibody at a time. Gold nano particles with antibodies are provided on a porous pad within a pre-reaction chamber 34, along with silver ions (for example silver nitrate) while 25(OH)D is coated onto a suitable substrate, such as a silicon-based substrate, in the reaction chamber 26. When blood plasma reaches the pre-reaction chamber 34, the AuNP-antibody reacts with 25(OH)D first; unreacted AuNP-antibodies are then carried into the reaction chamber 26 and are captured by the 25(OH)D that is coated onto the surface, generating a characteristic colour, which is amplified by the presence of silver ions.

10. Vitamin B12—the detection may be based on the use of a highly stable RNA aptamer, deposited on a porous pad in the reaction chamber 26 during assembly. This RNA aptamer binds to vitamin B12. It involves a structural modification of 2'-hydroxyl group of ribose to 2'-fluoro in all pyrimidines indicated in lowercase in the 35-mer aptamer: (5' GGA Acc GGu GcG cAu AAc cAc cuc AGu GcG AGc AA 3'). Aggregation of AuNPs is specifically induced by desorption of the RNA aptamer from the surface of AuNPs as a result of the interaction between the aptamer and the vitamin B12, leading to the colour change from red to purple.

It will be appreciated that the various colorimetric reactions described above are by way of example only, and that other colorimetric reactions may be used instead. It will also be appreciated that a device of the invention may monitor only a selection of the various biomarkers discussed above, but preferably at least six different biomarkers.

It will be appreciated from the above description and drawings that some of the microfluidic channels 24 include pre-reaction chambers 34. These act as mixing chambers, and are required in those cases where reagents must be mixed with the plasma before it reaches the reaction chamber 26. They also provide some delay in the timing with which the plasma reaches the reaction chamber 26, which in some cases may be advantageous.

The invention claimed is:

1. A device for enabling a user to detect biomarkers, the device comprising:

an element that defines a multiplicity of microfluidic channels that communicate between an inlet duct and an outlet duct;

the inlet duct communicating with an inlet port at a surface of the element into which a user can introduce a drop of body fluid;

the outlet duct communicating with an outlet port at a surface of the element, the device also incorporating a resilient elastomeric bladder connected to the outlet port to provide suction;

wherein each microfluidic channel defines a reaction chamber containing a biomarker-sensitive reagent which provides a colour or a change of colour in the presence of a biomarker, there being a multiplicity of different biomarker-sensitive reagents, one such biomarker-sensitive reagent being provided in each of the multiplicity of different microfluidic channels, each microfluidic channel enclosing a porous hydrophobic element downstream of the reaction chamber, and at least part of the element being transparent so that the colour or change of colour within the reaction chamber can be viewed from outside the element; and a cover, the cover defining multiple lenses that are above the reaction chambers, and the cover also comprising an openable flap that covers the resilient elastomeric bladder, wherein the openable flap holds the resilient elastomeric bladder in a compressed state such that when the openable flap is opened, the resilient elastomeric bladder expands to provide said suction.

2. A device as claimed in claim 1 wherein each microfluidic channel has a transverse dimension no more than 100 µm.

3. A device as claimed in claim 1 wherein the inlet duct also incorporates a filter.

4. A device as claimed in claim 3 wherein the filter element is longer in the flow direction than its thickness.

5. A device as claimed in claim 3 wherein the filter element is of thickness 50 µm, of width 4 mm, and of length 2 mm.

6. A device as claimed in claim 1 wherein the lenses are square lenses, each of which is convex on its lower surface and flat on its upper surface.

7. A device as claimed in claim 1 wherein the inlet port has a capacity in the range 20 to 50 µL.

8. A device as claimed in claim 1 wherein the element is of laminated construction, comprising a white substrate below the microfluidic channels, with a transparent material covering the microfluidic channels.

9. A device as claimed in claim 1 wherein the cover also defines an aperture aligned with the inlet port.

10. A method for analysis of a body fluid, using the device as claimed in claim 1 to detect biomarkers.

11. The method as claimed in claim 10 wherein the device is used in conjunction with a smart phone that includes a camera, the camera being used to view the colours of the reaction chambers, as viewed through the cover where this is provided.

12. The method as claimed in claim 11 wherein the smart phone is used to record the information about the colours.

13. The method as claimed in claim 11 wherein the smart phone is used to deduce from the observed colours information about each of the biomarkers.

14. A method for liquid analysis, using the device as claimed in claim 1 to detect multiple biomarkers by colorimetric reactions, wherein the biomarkers are selected from: lipids, glucose, HbA1c (i.e. glycated haemoglobin), creatinine, haemoglobin, uric acid, gamma GT (i.e. gamma glutamyl transferase), vitamin D, vitamin B 12, and folic acid.

15. A method as claimed in claim 14 wherein at least six such biomarkers selected from: lipids, glucose, HbA1c (i.e. glycated haemoglobin), creatinine, haemoglobin, uric acid, gamma GT (i.e. gamma glutamyl transferase), vitamin D, vitamin B12, and folic acid, are selected and detected, so a plurality of lifestyle diseases can be monitored.

16. An apparatus comprising:
   a device as claimed in claim 1; and
   a smart phone that includes a camera, the camera adapted to view the colours of the reaction chambers.

17. An apparatus as claimed in claim 16, wherein the smart phone is adapted to record information about the colours.

18. An apparatus as claimed in claim 16, wherein the smart phone comprises a software application for analysing the colours to deduce information about each of the biomarkers.

* * * * *